US009938378B2

(12) United States Patent
Wellings

(10) Patent No.: US 9,938,378 B2
(45) Date of Patent: *Apr. 10, 2018

(54) CROSS-LINKED POLY-E-LYSINE NON-PARTICULATE SUPPORT

(75) Inventor: Donald Wellings, Runcorn (GB)

(73) Assignee: SPHERITECH LTD, Runcorn, Cheshire (GB)

( * ) Notice: Subject to any disclaimer, the term of this patent is extended or adjusted under 35 U.S.C. 154(b) by 511 days.

This patent is subject to a terminal disclaimer.

(21) Appl. No.: 14/112,742

(22) PCT Filed: Apr. 20, 2012

(86) PCT No.: PCT/EP2012/057271
§ 371 (c)(1),
(2), (4) Date: Jan. 23, 2014

(87) PCT Pub. No.: WO2013/041250
PCT Pub. Date: Mar. 28, 2013

(65) Prior Publication Data
US 2014/0142198 A1    May 22, 2014

(30) Foreign Application Priority Data

Apr. 20, 2011   (GB) .................................. 1106742.8

(51) Int. Cl.
| | |
|---|---|
| *C08G 69/48* | (2006.01) |
| *A61L 15/32* | (2006.01) |
| *C08J 3/12* | (2006.01) |
| *C08J 3/24* | (2006.01) |
| *C12N 11/02* | (2006.01) |
| *C12N 11/06* | (2006.01) |
| *A61L 26/00* | (2006.01) |
| *G01N 33/532* | (2006.01) |
| *G01N 33/543* | (2006.01) |
| *G01N 33/58* | (2006.01) |
| *C07H 21/00* | (2006.01) |
| *C07K 1/04* | (2006.01) |
| *C08B 37/00* | (2006.01) |
| *C12N 5/00* | (2006.01) |
| *C12N 11/08* | (2006.01) |
| *C09D 177/04* | (2006.01) |

(52) U.S. Cl.
CPC .............. *C08G 69/48* (2013.01); *A61L 15/32* (2013.01); *A61L 26/0019* (2013.01); *A61L 26/0047* (2013.01); *C07H 21/00* (2013.01); *C07K 1/042* (2013.01); *C08B 37/00* (2013.01); *C08J 3/126* (2013.01); *C08J 3/24* (2013.01); *C09D 177/04* (2013.01); *C12N 5/0018* (2013.01); *C12N 11/02* (2013.01); *C12N 11/06* (2013.01); *C12N 11/08* (2013.01); *G01N 33/532* (2013.01); *G01N 33/54313* (2013.01); *G01N 33/585* (2013.01); *A61L 2300/434* (2013.01); *C08J 2477/00* (2013.01); *Y10T 428/249991* (2015.04); *Y10T 428/2998* (2015.01)

(58) Field of Classification Search
None
See application file for complete search history.

(56) References Cited

U.S. PATENT DOCUMENTS

| 8,105,619 B2 | 1/2012 | Odermatt et al. |
| 2003/0103931 A1 | 6/2003 | Takasaki et al. |
| 2008/0292671 A1 | 11/2008 | Ho et al. |
| 2008/0319101 A1 | 12/2008 | Nakajima et al. |
| 2010/0161021 A1 | 6/2010 | Iino et al. |

FOREIGN PATENT DOCUMENTS

| CN | 1850301 A | 10/2006 |
| EP | 1 967 217 A2 | 9/2008 |
| EP | 2 210 917 A1 | 7/2010 |
| JP | S61-205864 A | 9/1986 |
| JP | H01-126557 A | 5/1989 |
| JP | H05-501543 A | 3/1993 |
| JP | H08-502498 A | 3/1996 |
| JP | H10-501706 A | 2/1998 |
| JP | H11-152330 A | 6/1999 |
| JP | 2000-070356 A | 3/2000 |
| JP | 2001-126557 A | 5/2001 |

(Continued)

OTHER PUBLICATIONS

Merrifield, 1973, chapter 16, 'Chemistry of Polypeptides', pp. 335-361, edited by Katsoyannis.*
Website: https://en.wikipedia.org/wiki/Carbodiimide, Last modified Sep. 2005, 4 pages.*
Advances in Immunology, vol. 5, Academic Press, Jan 1, 1966—Medical—p. 105.*
Molecular Microbiology (2006), 60, (5), 1091-1098.*
Kato, Biomaterials 24 (2003) 4253-4264.*
Kokufuta, Colloids and Surfaces B: Biointerfaces 87 (2011) 299-309.*
Kawai, 2006, Journal of Macromolecular Science, Part B: Physics, 17:4, 653-681.*
Baldaro et al., "Pen G acylase catalyzed resolution of phenylacetate esters of secondary alcohols" Tetrahedron: Asymmetry, May 1993, pp. 1031-1034, vol. 4, issue 5.
Carleysmith et al., "Deacylation of benzylpenicillin by immobilized penicillin acylase in a continuous four-stage stirred-tank reactor" Biotechnology and Bioengineering, Jun. 1979, pp. 1057-1073, vol. 21, issue 6.
Kawai et al., "Conformational effects on complex formation in polymeric systems and matrix polymerization", Journal of Macromolecular Science, Physics, 1980, pp. 653-681, vol. B17, No. 4.

(Continued)

*Primary Examiner* — Satyanarayana R Gudibande
(74) *Attorney, Agent, or Firm* — Lathrop Gage LLP; Brian C. Trinque

(57) ABSTRACT

The invention provides a non-particulate cross-linked poly-ϵ-lysine polymer. The poly-ϵ-lysine and cross linker are linked by amide bonds and may the cross linker has at least two functional groups capable of reacting with an alpha carbon amine of poly-ϵ-lysine. The polymer is suitably insoluble in water and other solvents and is provided in macro form for example a sheet, article or fiber. The macro form polymer is useful in a wide range of applications including wound treatment, as a medical diagnostic comprising a particulate support and a functional material bound or retained by the support and solid phase synthesis of peptides, oligonucleotides, oligosaccharides, immobilization of species, cell culturing and in chromatographic separation.

23 Claims, 8 Drawing Sheets

(56) References Cited

FOREIGN PATENT DOCUMENTS

| | | | |
|---|---|---|---|
| JP | 2001-128659 | A | 5/2001 |
| JP | 2003-171464 | A | 6/2003 |
| JP | 2003-176353 | A | 6/2003 |
| JP | 2005-053974 | A | 3/2005 |
| JP | 2006-307004 | * | 11/2006 |
| JP | 2006-307004 | A | 11/2006 |
| WO | 1990/013256 | A1 | 11/1990 |
| WO | 1991/008770 | A1 | 6/1991 |
| WO | 1994/010191 | A1 | 5/1994 |
| WO | 1995/026761 | A1 | 10/1995 |
| WO | 2001/070291 | A1 | 3/2001 |
| WO | 2007/028607 | A2 | 3/2007 |
| WO | 2007/061058 | A1 | 5/2007 |
| WO | 2008/012064 | A1 | 1/2008 |
| WO | 2009/057802 | A1 | 5/2009 |
| WO | 2011/009539 | A1 | 1/2011 |
| WO | 2011/032705 | A2 | 3/2011 |

OTHER PUBLICATIONS

International Search Report with Written Opinion corresponding to International Patent Application No. PCT/EP2012/057271, dated Aug. 8, 2012.
Search Report corresponding to Great Britain Patent Application No. 1106742.8, dated Aug. 23, 2011.
Oh et al. (1993) "Characteristics of an Immobilized Form of Transglutaminase: A Possible Increase in Substrate Specificity by Selective Interaction with a Protein Spacer," J. Agric. Food Chem. 41:1337-1342.
Russo (2008) "Reductive Glutaraldehydation of Amine Groups for Identification of Protein N-termini," J. Proteome Red. 7(9):4178-4182.
International Preliminary Report on Patentability corresponding to International Patent Application No. PCT/EP2012/057264, dated Oct. 22, 2013.
International Search Report with Written Opinion corresponding to International Patent Application No. PCT/EP2012/057264, dated Aug. 8, 2013.

* cited by examiner

CROSS-LINKED POLY-∈-LYSINE NON-PARTICULATE SUPPORT

RELATED APPLICATIONS

This application is a 35 U.S.C. § 371 filing of International Application No. PCT/EP2012/057271, filed Apr. 20, 2012; which claims priority to Great Britain Patent Application No. 1106742.8, filed on Apr. 20, 2011. The entire contents of each are incorporated herein by reference.

This invention relates to a non-particulate polymeric support, a method of preparing the support and the use of the support in a solid phase process. In particular, the invention relates to a non-particulate polymeric support comprising cross-linked poly-∈-lysine especially to a cross-linked poly-∈-lysine support in macro form. The support is useful in a wide range of physical and chemical processes especially where interaction with a substrate is required for example solid phase synthesis, solid phase extraction, solid phase reagents, immobilization of species, cell culture, catalysis, chromatography, wound management and in medical diagnostics.

For the purpose of this invention the term polymer support is used to describe the polymer in any form such as a monolith, a membrane, a fiber by way of examples with the exception of a particulate version.

Poly-∈-lysine is a naturally occurring short chain polydispersed polyamide consisting of the amino acid lysine linked through amide bonds between the carboxyl and the epsilon (∈) amino group. This structure is unusual in that the amide bonds are formed between the carboxyl and ∈ amino groups of lysine whereas a normal peptide bond between amino acids in a peptide and traditionally employed poly-lysine, is formed between the carboxyl and a amino groups. The polydispersity in naturally occurring poly-∈-lysine is typically between 25-35 amino acids. In traditional commercially available poly-lysine the peptide has a much broader poorly controlled polydispersity typically containing anything from 5-500 amino acids.

Cross-linked poly-∈-lysine structurally has a more elastic nature than traditional poly-lysine due to the greater chain length between the amide bonds. Structurally poly-∈-lysine is effectively an α-amino Nylon 5.

Poly-∈-lysine is currently manufactured by bacterial fermentation on a large scale as a food preservative. It is inexpensive and readily available in commercial quantities. In this invention we describe the cross-linking of Poly-∈-lysine to form insoluble polymeric supports that have applications across a range of technologies. These include but are not limited to solid phase peptide synthesis, solid phase oligonucleotide synthesis, solid phase extraction, solid phase reagents, immobilization of species, cell culture, catalysis, chromatography, slow release of agrochemicals, and slow release of pharmaceuticals, regenerative medicine and medical diagnostics.

Solid support materials useful in solid phase synthetic processes are known. A wide range of physical and chemical processes employ solid support materials including by way of example synthesis of organic molecules, in particular peptides and oligonucleotides, immobilization of species, support of catalysts, ion exchange, extraction of species from a material, diagnostics and chromatography.

Typically, multi-stage synthesis of an organic molecule involves numerous isolation steps to separate intermediates, produced at each stage, before progressing to the subsequent stage. These processes are often time-consuming, expensive and may be inefficient as regards yield. The intermediates often require purification to remove excess reagents and reaction by-products and procedures such as precipitation, filtration, bi-phase solvent extraction; solid phase extraction, crystallization and chromatography may be employed.

Solid phase synthesis offers some advantages over solution phase synthesis. For example, isolation procedures used in solution phase synthesis may to some extent be avoided by reversibly attaching the target molecule to a solid support. Excess reagents and some of the side-products may be removed by filtration and washing of the solid support. The target molecule may be recovered in essentially quantitative yield in some processes which is typically particularly difficult in solution phase synthesis. In addition, the time required to perform operations on a solid support is typically much less than that required carrying out the equivalent stage in a solution phase synthesis.

Immobilization of species in a range of processes is also known. For example, polymer supports are commonly used for the immobilization of catalysts for use in traditional organic chemistry including chemo and bio catalysis. Immobilized enzymes may be employed to perform organic chemical reactions or for chiral resolution, for example the use of immobilized Penicillin amidase for the resolution of secondary alcohols (E. Baldaro et al. Tet. Asym. 4, 1031, (1993) and immobilized Penicillin G amidase is also used for the hydrolysis of Benzylpenicillin in the manufacture of Amoxicillin (Carleysmith, S. W. and Lilly, M.D. Biotechnol. Bioeng., 21, 1057-73, 1979).

Solid supports are also used to immobilize biological macromolecules for medical and diagnostic applications. This includes immobilization of proteins, monoclonal and polyclonal antibodies. Cell culture is commonly carried out on solid supports with specific surface characteristics and morphology. Immobilized enzymes on the supports can also be employed as sensors to generate a signal. An example is the detection of glucose by the glucose oxidase/peroxidase coupled enzyme system, in which the presence of glucose generates hydrogen peroxide which in turn is the substrate for peroxidase for the oxidation of a wide variety of substrates to provide a coloured, fluorescent or luminescent signal.

A variety of fluors whose fluorescence is sensitive to specific cations or anions may be utilized to indicate concentrations of specific ions including hydrogen ions for pH measurement.

Polymeric materials are often used in chromatography where the solid supports are termed stationary phases. In certain modes of chromatography the cost of stationary phases may be restrictive. In other modes the physical nature of the stationary phase can reduce the effectiveness of the technology. For instance, the soft polymers often used for affinity, ion-exchange and gel permeation chromatography cannot be used at high flow rates because of the deformable nature of the particles. The rigid macroporous polymers used for many other modes of chromatography can often be mechanically friable and subsequently suffer from a short lifetime.

The application of solid supports or stationary phases in chromatographic separations is very extensive for example complex high-technology separations used in the pharmaceutical and biotechnology industry and larger scale processes used in the mining industry. Some of the pharmaceutical industry's most valuable drugs are purified by preparative chromatography and improved chromatographic separation would be technically beneficial and economically advantageous. In the mining and precious metal recovery industry a large portion of the world's palladium, a critical component in a wide range of industrial applications and processes including catalytic converters and manufacture of high value products, may be refined using immobilized crown ethers (Traczyk, F. P.; Bruening, R. L.; Izatt, N. E. "The Application of Molecular Recognition Technology (MRT) for Removal and Recovery of Metal Ions from Aqueous Solutions"; In Fortschritte in der Hydrometallurgie; 1998, Vorträge beim 34. Metallurgischen Seminar des Fachausschusses fuer Metallurgische Aus-und Weiterbildung der GDMB; 18-20 Nov. 1998; Goslar).

The use of polymeric materials in solid phase extraction and in the preparation of solid phase reagents is also known in the chemical, pharmaceutical and biotechnology industry.

Known solid phase supports generally comprise polymeric materials of a physical nature to suit the application. For ease of use these polymeric materials are often monolithic.

In peptide synthesis, polystyrene is widely employed as a polymer support for supporting the growing peptide and is relatively low-cost, widely available and provides acceptable performance in peptide synthesis. Other commercially available supports commonly used for solid phase synthesis of peptides and oligonucleotides may be expensive, for example due to the complex manufacturing processes. Microporous polymers and macroporous polymers are generally used. Microporous polymers have a relatively low level of cross-linker which allows the polymer particles to solvate and consequently swell in suitable solvents. Macroporous polymers often have a high level of cross-linker in the polymer matrix and contain large pores. These polymeric materials are generally rigid and have good flow characteristics and are suitable for use in packed columns.

A need remains to find an alternative or improved and cost-effective polymer suitable for use as a non-particulate support, for example a monolithic support in a wide range of applications. We have now found that a cross-linked poly-ϵ-lysine polymer provides an excellent combination of characteristics, may be tailored according to the desired properties by appropriate selection of the cross-linker and may be employed in a wide-range of applications cost-effectively.

In a first aspect, the invention provides a non-particulate cross-linked poly-ϵ-lysine polymer.

The non-particulate cross-linked poly-ϵ-lysine polymer is preferably in macro form. The term "macro form" means that the polymer is formed in a non-particulate form and is monolithic and has a form which is capable of being used or handled as a single entity as opposed to, in particulate form, requiring multiple particles for effective use. Examples of macro forms include a sheet, a fibre and an article, for present purposes an article having a significant length in all three dimensions as opposed to a fibre having a significant length in one dimension and a sheet in two dimensions.

The non particulate polymer may contain pores. The size and distribution of pores may be tailored according to the intended use. Preferably, the non particulate polymer contains macropores, micropores or supermacropores or is in the form of a microporous hydrogel or a fibre.

The invention also provides a non-particulate support comprising a cross-linked poly-ϵ-lysine polymer according to the first aspect of the invention.

Preferably the cross linker renders the poly-ϵ-lysine insoluble. The non-particulate cross-linked poly-ϵ-lysine polymer is particularly useful in providing a support for a wide-range of applications especially where the cross-linking provides a polymer which is insoluble in water and other solvents. Where lower levels of cross-linking are employed, the polymer may be soluble in water and this provides advantage in certain applications as described below. Suitably the polymer comprises poly-ϵ-lysine and a cross linker linked by amide bonds.

The poly-ϵ-lysine component of the cross-linked poly-ϵ-lysine is the principle component of the cross-linked polymer. The cross-linker acts to bond poly-ϵ-lysine polymers together such that the poly-ϵ-lysine polymers provide a structure, for example a lattice for use in a range of applications including support for synthesis of organic molecules, for example polypeptides and polynucleotides, chromatography, use as a support for functional materials as described herein below.

The poly-ϵ-lysine polymer is suitably cross-linked by reacting a cross-linker having at least two functional groups, preferably two or more carboxylic acid groups, able to react with the free alpha (α) amino groups in the poly-ϵ-lysine polymer. The cross-linker may have three or more functional groups to link to the same number of poly-ϵ-lysine polymer chains or fewer chains but with multiple links to one or more such chains. The cross-linker may contain other functional groups which do not participate in the cross-linking reaction and remain available for reaction with other species during use of the cross-linked polymer.

The level of cross-linking in the polymeric support can be used to control the physical form and chemical reactivity of the final cross-linked poly-ϵ-lysine. Introduction of high levels of cross-linking will produce rigid structures suitable for the preparation of macroporous polymer supports, whereas a low level of cross-linking will produce softer more microporous materials. The amine functionality is high with low levels of cross-linking, which can be readily tailored by controlled capping. The handling, solvation and physical properties can also be defined by the type of cross-linker introduced.

Suitably the cross-linker comprises a specific compound or group of compounds. The cross-linker may comprise a repeat unit and be polydisperse however, the polydispersity is narrow to ensure appropriate control over the lattice structure formed upon cross-linking. The cross-linker comprises at least two functional groups capable of reacting with an alpha carbon amine of poly-ϵ-lysine. Examples of common functional groups suitable for this purpose include carboxylic acids.

Amide bonds are biodegradable and the cross-linked polymer of the invention and supports comprising it are especially useful in applications in which biodegradability is important. Further, amide bonds may be metabolized for example by enzymes including proteases, as well as being biodegradable and are particularly advantageous for use in medical applications and especially medical use on or in the human or animal body. The polymers and supports of the invention provide benefit in medical applications where the polymer or support suitably degrades over time thereby avoiding the need for procedures to remove the support after its function has been completed.

In an especially preferred embodiment, the bonds between the cross-linker and the poly-ϵ-lysine comprise amide bonds, preferably at least 20%, more preferably at least 50%, desirably at least 90% and especially substantially all of the bonds are amide bonds.

In a further preferred embodiment, the polymer is lightly cross-linked and from 1 to up to 50%, 1 to 20% and 1 to 10% of the epsilon amine groups are cross-linked. Lightly cross-linked polymers and supports of the invention are especially useful in synthesis of organic species, for example peptides and nucleotide sequences, and in delivery of active species, for example pharmaceutically active agents.

Accordingly, in a preferred embodiment, the cross-linker comprises two or more carboxylic acid groups and an aliphatic chain linking the two or more groups. The cross-linker may comprise a polyacid. In a preferred embodiment, the cross-linker comprises a compound of formula X[CO$_2$H]$_n$ where n is 2 or more, preferably 2 to 6 more preferably 2 to 4 and X is a hydrophobic or hydrophilic linking group, preferably aliphatic. Suitably group X has a molecular weight of 14 to 250, more preferably 28 to 140 excluding any functional substituents on the linking group. X may contain heteroatoms for example oxygen and nitrogen as part of the backbone of the linking group and may contain functional groups for reaction with other species during use of the cross-linked poly-ε-lysine polymer.

The aliphatic chain linking the acid groups may be hydrophilic, preferably a bis-carboxy-polyalkylene glycol, for example bis-carboxy-polyethyleneglycol, or the aliphatic chain may be hydrophobic providing a hydrophobic cross-linker, for example, sebacic acid provides a more lipophilic support. The cross-linker may be derived from a precursor material, for example an anhydride. Examples of other suitable cross-linkers include nitrilotriacetic acid, glutaric acid and HOOCCH$_2$CH$_2$CONHCH$_2$CH$_2$OCH$_2$CH$_2$OCH$_2$CH$_2$ OCH$_2$CH$_2$NHCO CH$_2$CH$_2$COOH.

The physical integrity of the non-particulate support or macro form may deteriorate or be lost where the cross-linker has a chain length of fewer than 5 atoms. In a preferred embodiment, X comprises a hydrocarbyl group and comprises only hydrogen and carbon atoms, preferably 3 to 14, more preferably 6 to 12 and especially 6 to 8 carbon atoms. Preferably the cross linker has 8 to 10 carbon atoms. The hydrocarbyl group may be linear or branched, preferably linear. The hydrocarbyl group may be saturated or unsaturated, preferably saturated. Examples of preferred cross-linkers include di-carboxylic acids having 8 to 10 carbon atoms such as sebacic acid and azelaic acid.

The poly-ε-lysine may be derivatised or modified prior to cross-linking to allow other cross-linking chemistry familiar to those skilled in the art. For example, the poly-ε-lysine can be derivatised or modified prior to cross-linking to allow other cross-linking chemistry familiar to those skilled in the art. For example the poly-ε-lysine could be pre-derivatised by reaction with glutaric anhydride then cross-linked using multi-functional amines using the activation chemistry described herein.

The poly-ε-lysine may be cross-linked using an amino acid for example aspartic acid and glutamic acid. The cross-linked poly-ε-lysine in this case would only generate naturally occurring amino acids only upon degradation. Reaction with cystine for example would produce a polymer cross-linked in a similar way but in this instance the structure would contain a cysteine disulfide bridge, which again on degradation would generate naturally occurring amino acids.

Examples of preferred cross-linkers include glutamic acid, cystine, EDTA (ethyenediaminetetraacetic acid), adipic acid, dodecanedioic acid, synthetic peptides especially peptides based upon the structure of natural collagen, synthetic peptides containing the tripeptide sequence -Arg-Gly-Asp-, the cell binding peptide in fibrinogen and other natural proteins, naturally occurring polymers that contain multiple carboxylic acid groups including gelatin, alginic acid and crown ethers with multiple carboxylic acids especially suitable for use in metal chelation and chromatography. Further suitable examples are shown below:

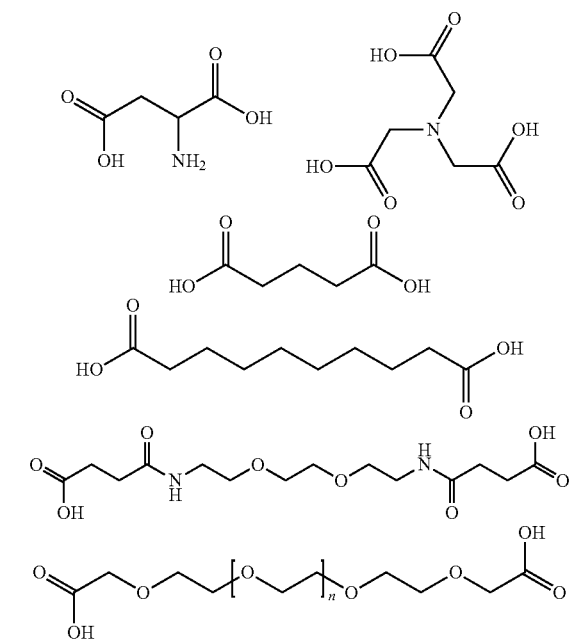

Whilst the polydispersity of the poly-ε-lysine is not critical, in a preferred embodiment the polydispersity of the poly-ε-lysine is suitably from 10 to 50 and preferably between 25-35 amino acids. A narrower polydispersity allows for more precise control over the ultimate properties of the cross-linked polymer support. Cross-linked poly-ε-lysine will have many applications for example in several modes of chromatography but may be of particular advantage for chiral separations due to the repeating L-chiral centers along the chain. The pendant a amino groups can be readily modified to incorporate other chromatographic binding sites or other chiral moieties that will impart a range of chiral selective properties on the support.

Suitably, the relative amount of poly-ε-lysine and cross linker are selected such that the poly-ε-lysine is the principle component of the cross-linked poly-ε-lysine polymer. Where a fully cross-linked polymer is required, the relative amounts of poly-ε-lysine polymer and cross linker will be selected to provide stoichiometric molar equivalents as regards the alpha amine groups of the poly-ε-lysine and the cross-linking functional groups. Where amine functionality is desired, a corresponding lower amount of cross-linker is employed to provide the desired proportion of free amine groups. Suitably the cross-linked poly-ε-lysine polymer has from 0 to 95% of its alpha amine groups as free amine groups. In a preferred embodiment in which a relatively large proportion of the amine groups for example 50 to 100%, have been reacted, the cross-linked poly-ε-lysine polymer will suitably exhibit relatively rigid characteristics. Where a minor proportion of the amine groups have been reacted to provide cross-linking, for example from 5 to up to 50% of the amine groups, the polymer is suitably relatively soft or gel-like. Soft or gel-like polymers are especially useful in the synthesis of polypeptides, particularly long polypeptides.

In a preferred embodiment, the cross-linked poly-ε-lysine polymer comprises from greater than 0.001 to 20 mmol/g, 0.01 to 10 mmol/g of cross-linked poly-ε-lysine polymer, preferably from 0.1 to 8 mmol/g and more preferably from 1 to 8 mmol/g especially for polypeptide synthesis for example from 1 to 3 mmol/g.

In another embodiment, the cross-linked poly-ε-lysine polymer comprises from 0.01 to 0.3 mmol/g, particularly advantageous for the synthesis of nucleic acid sequences.

The cross-linked poly-ε-lysine polymer may be reacted further to provide particular functionality for a given application. Suitably, the polymer is reacted with a compound having at least three functional groups, two for reacting with the polymer to provide cross-linking between two polymer chains and the other to provide free functionality for use in the desired application.

The cross-linked poly-ε-lysine support may be further functionalised, for example by conversion to a carboxylic acid using succinic acid as desired. By way of example, an amine functionalised support may be treated with N-hydroxysuccinimide and 1-Ethyl-3-[3-dimethylaminopropyl] carbodimide hydrochloride in preparation of an activated polymer for immobilising a protein, for example protein A.

The cross-linked poly-ε-lysine polymer may contain an excess of the cross-linker to provide carboxyl functionality for a given application.

The non-particulate polymeric may typically be made by a dispersion or emulsion polymerization process in which a solution of monomers is dispersed in an immiscible solvent (continuous phase) prior to initiation of the polymerization. The mix of poly-ε-lysine and cross-linker and polymerisation components, for example a catalyst and initiator are suitably mixed and cast into the desired macro form, for example a sheet or article or may be spun into a fibre. In the case of fibres, the polymer may be cross linked after the fibres of poly-ε-lysine have been spun or cross-linking may occur before or during cross-linking. Typically then filtered, washed and classified to isolate the required particle size distribution.

The non-particulate polymer of the invention may be porous, preferably macroporous or microporous. These terms are known to the person skilled art.

The term "macroporous" refers to polymers which are typically relatively highly cross-linked and rigid. A macroporous polymer typically has pores in the Angstrom range (1-5000 Å, that is 0.1 to 500 nm.

The term "microporous" refers to polymers which have a relatively low level of cross-linked material and which may not have pores as such but solvate and swell to form gels in an appropriate solvent, for example a microporous hydrogel. Microporous polymers or supports according to the invention are desirably of such a size as to provide a translucent or preferably transparent polymer.

The term "supermacroporous" refers to polymers which are usually highly cross-linked but have much larger pores than a macroporous polymer for example a sponge. The pores typically are of the micron to mm order of magnitude, typically 0.5 um up to 1 mm. Suitably polymers or supports of the invention for cell culture have pores from 20 um to 500 um.

It is possible to produce products which may have one size of pores or characteristic s but the polymer from which the product is made may have smaller pores. For example a supermacroporous product having pores in the micron to mm scale may be made from a polymer which microporous or macroporous. In Example 1 below, the product is supermacroporous but the actual polymer is microporous.

A polymer or support according to the invention suitably comprises voids of 10 to 500 microns, for example 10 to 100 microns. In a preferred embodiment, the macroporous polymer comprises voids of 50 to 300 microns and more preferably 100 to 200 microns.

The invention is particularly useful in supporting precious metal catalysts, for example palladium catalysts. A particularly advantageous example is palladium acetate supported on cross-linked poly-ε-lysine functionalized to form a carboxylic acid.

The support may be employed in applications involving electro-conducting and light emitting polymers. The support containing light emitting polymers may be arranged on display panels.

The polymer support is particularly useful for solid phase synthesis of an organic species, particularly macromolecules. In a preferred embodiment the polymer support may be employed in the synthesis of peptides, oligonucleotides or oligosaccharides.

The invention further provides for the use of a monolithic polymer support according to the invention as a solid phase in a chromatography process.

The polymer support of the invention is also useful for solid phase extraction to remove species from a liquor which is contacted with the support, whether in batch form or as a flow over the support, for example ion extraction and ion exchange.

The support of the invention may be used to immobilize species including antibodies, oligonucleotides, enzymes or fluors and may be positioned in an array, with each support assaying a different component of a solution. Polymers having ligands covalently attached to their surface, or via polymers bound to the surface may be employed as 'wells'. Specific binding of a target ligand such as antigen or complimentary DNA or RNA sequence may then be detected using established methods.

The monolithic polymer support of the invention also may be employed to immobilize a biocatalyst or whole cells for use in biocatalysis. Biocatalysts are often used in columns or in systems with filter plates for separation of the solid phase from the mixture under extraction.

The monolithic polymer support of the invention is especially useful in immobilizing species including solid phase reagents, metal and other catalysts, biocatalysts, enzymes, proteins, antibodies including polyclonal and monoclonal antibodies, whole cells and polymers. The invention is particularly advantageous in supporting enzymes, for example the lipase Cal B. *Lipase* Cal B may be employed in a transesterification process.

The invention further provides for a method of enzymatic manufacture of biodiesel using the support or polymer of the invention.

The present invention is also especially useful in the immobilisation of affinity ligands such as Protein A. Protein A is suitably used in the purification of monoclonal antibodies.

In a further application, the polymer support of the invention may also be used in chemocatalysis, for example by immobilizing transition metal catalysts and ligands.

In yet a further application, the present invention may be used in cell culture. Mass culture of animal cell lines is fundamental to the manufacture of viral vaccines and many products of biotechnology. Biological products produced by recombinant DNA technology in animal cell cultures include enzymes, synthetic hormones, immunobiologicals (monoclonal antibodies, interleukins, lymphokines) and anticancer agents. Many simpler proteins can be produced using rDNA in bacterial cultures; more complex proteins that are glycosylated (carbohydrate-modified) currently must be made in animal cells. An important example of such a complex protein is the hormone erythropoietin. The cost of growing mammalian cell cultures is high, so companies are constantly looking to improve techniques.

Cells can be grown in suspension or as adherent cultures. However, adherent cells require a surface, which may be coated with extracellular matrix components to increase adhesion properties and provide other signals needed for growth and differentiation. Generally cells derived from solid tissues are adherent. Organotypic culture involves growing cells in a three-dimensional environment as opposed to two-dimensional culture dishes. This 3D culture system is biochemically and physiologically more similar to in vivo tissue, but is technically challenging to maintain because of many factors (e.g. diffusion). Gelatin is hydrolyzed collagen where inter and intra chain amide bonds have been hydrolyzed chemically to form soluble peptide chains. Collagen is an ideal and natural environment for cells to adhere and differentiate. The poly-ε-lysine may also be co-polymerized with other proteins, for example gelatin to form a collagen like environment.

In a further aspect, the invention provides for the use of a polymer, macroporous or microporous support or coating according to the invention to culture cells preferably on the surface of the support or coating. Suitably, stem cells may be cultured on the polymer support of the invention to reduce uncontrolled differentiation and to control desired differentiation.

In an especially preferred embodiment, the invention is beneficial for use in wound care. Chronic wounds are exacerbated by metallino-proteases which can be rendered inactive by polymer particles that chelate metal ions required by the enzyme. The cross-linked poly-ε-lysine, preferably capped with metal chelating species are suitable for use in this application.

The invention provides for the use of non-particulate cross-linked poly-ε-lysine or a monolithic support comprising cross-linked poly-ε-lysine as a wound treatment product or component thereof. The wound treatment product may comprise a flexible article but preferably comprises a self-supporting article. The wound treatment product suitably comprises a polymer or particulate support according to the invention and a component or a composition for treating a wound and/or a therapeutic agent.

Where reference is made herein to the polymer of the invention as regards suitable uses, the support of the invention is also suitable for such uses unless otherwise stated.

In a preferred embodiment, the invention provides a sheet comprising a cross-linked poly-ε-lysine having micropores, macropore or supermacropores sheets of for use in wound management. These sheets can be used internally following post-operative surgery as patches to prevent adhesion. Similarly, the polymer can be used in-vivo to promote tissue regeneration.

These sheets can also be used for applications in external wound management. Some advantages of the polymer described in this invention lies in the biocompatibility, the porosity, the hydrophilic nature and the ease of chemical modification. Chemical modification allows attachment of other species such as cell binding proteins, cell binding peptides, or anticoagulant peptides by way of examples.

Particular advantages from the polymer described in this invention result from its biocompatibility and in some circumstances the potential to be bioresorbed in-vivo to produce naturally occurring substances upon enzymatic degradation.

Sheets of the polymer have potential uses in sanitary applications, for example as an absorbent in nappies. Another example for application of the polymer in sheet form would be delivery of antibiotic, antimicrobial and antifungal agents for feminine healthcare. In particular, the polymer sheets themselves may have useful antiseptic properties since poly-ε-lysine has antibacterial and antifungal properties. The cross-linkers sebacic acid and dodecanedioic acid are also antiseptic so polymer sheets with excess cross-linker may also have antiseptic properties and are preferred.

The invention is particular useful in medical diagnostic tests such as immunoassay. Accordingly the invention further provides medical diagnostics for detecting the presence of a compound comprising a polymer according to the invention and a functional material such as an enzyme, for example horseradish peroxidase, supported by the polymer in the support for selectively reacting with or binding to the compound to be detected.

Many medical diagnostics rely upon solid supports to immobilize various diagnostic ligands. The polymer support of the present invention may be used in a medical diagnostic procedure where physical separation of the solid phase through a liquid phase.

In a further application, the polymer support may be used as an absorbent. The polymer support may be used to absorb household spillages, for example tea, coffee and wine, or may be used in larger-scale applications for example, to absorb oil from spillages. The absorbent support may be used to absorb the spillage and then left to biodegrade or, in the case of oil spillage in a body of water, effectively trap the oil and retain the oil in a buoyant mass for collection and disposal. Advantageously, the cross-linked poly-ε-lysine is biodegradable facilitating disposal with reduced environmental impact.

The polymer support of the invention may be used as a biodegradable carrier to carry a compound which is to be released over a period of time, for example a pharmaceutical or agrochemical compound or composition. This use provides a means of tailoring a dosage regime of the compound according to the loading of the compound in the support. In the case of a pharmaceutical, this may be advantageous in assisting the correct dosage of an active, for example with continuous slow release rather than requiring a patient to take periodic large doses, for example in chemotherapy.

Suitably the support comprises micropores and may be prepared in clear form. The polymer may suitably provide a replacement polymer for optical applications including contact lenses and corneal bandages for example. The polymer may be cast in the form of a contact lens. In this form the polymer may provide an antibacterial and antifungal surface and could also be used for the slow release of drugs. The optical properties of the clear forms of the polymer may also have applications in optical instruments such as microscopes and telescopes.

The invention provides a method of producing a lens comprising combining poly-ε-lysine and a cross-linker in the presence of a polymerization catalyst and casting into a lens-shaped receptacle to produce a transparent microporous monolith.

Three dimensional macroporous structures have been prepared for a broad range of applications. These include but are not limited to porous monoliths as stationary phases for chromatography, porous discs for filtration of species, porous materials for electroosmotic pumps, solid supports for solid phase synthesis and other chemical transformations, insulating materials, porous membranes for use in fuel cell applications and multi-dimensional scaffolds for tissue engineering.

The problems associated with current technologies for preparation of 3D structures relate primarily to the inability to create well defined pore dimensions and interconnecting channels. In circumstances where pore dimensions are better defined the range of polymer types that can be applied is limited. PCT/EP2010/005699 describes a process for introduction of controlled pores with interconnecting holes in a macroporous polymer. The polymer described in this invention can also be presented in macroporous form using this technology and is described by way of example here. The polymer described in this invention could also be used to form other macroporous structures, for example, poly-HIPE's.

In one preferred embodiment the 3D structure are formed by self-assembly of the macroporous polymer.

In chromatographic applications the 3D structures are often referred to as monoliths. When monoliths are used for chromatographic applications the 3D structure replaces the traditional particulate stationary phase. In contrast to diffusion, which is the typical driving force for mass transfer within the pores of particulate stationary phases, this convective flow through the pores of a monolith enables a substantial increase in the separation speed of large molecules such as proteins for example. Typically, the monolithic material is prepared in a flat or tubular mould, the sheet or cylinder removed from the mould, and the porous polymer punched or sliced to obtain discs. The pores within these monoliths are incorporated by addition of porogens. In silica based monoliths for example the porogens are typically large molecules such as polyethylene glycols. In polystyrene based monoliths for example the porogen is often toluene. The porogens currently in use introduce a broad pore size distribution with ill-defined connectivity which is detrimental to the chromatographic performance of the monoliths. Monolithic columns made from the cross-linked poly-ϵ-lysine of the present invention are especially useful in chromatography and a wide range of chromatography applications, for example affinity, ion-exchange, reversed phase, normal phase and chiral chromatography.

Proton exchange membrane fuel cells, also known as polymer electrolyte membrane (PEM) fuel cells are a type of fuel cell being developed for transport applications for example. These PEM fuel cells use a special polymer electrolyte membrane which amongst its properties must yield to efficient convective flow that is dictated by uniform pore structure. The additional chemical and physical properties that can be uniquely applied using the technology described herein may provide added benefits in this field. The polymer of this invention may be readily modified to introduce a range of characteristics that would be applicable in this field.

A 3D macroporous polymer prepared using the polymer of the invention may also comprise a functional material supported by the polymer. Examples of suitable functional materials include a catalyst, an initiator species for peptide synthesis, a pharmaceutical active, an agrochemical active, a macromolecule, an enzyme, a nucleic acid sequence and a protein.

The invention is particularly useful in supporting precious metal catalysts, for example palladium catalysts. A particular advantageous example is palladium acetate supported on cross-linked poly-ϵ-lysine functionalized to form a carboxylic acid.

The chiral nature of the poly-ϵ-lysine may also impart a chiral selectivity to such catalysts.

The 3D macroporous polymer of the invention may be used in any chemical or physical process in which a solid support is used.

The 3D macroporous polymer or a polymer coating may be employed in applications involving electro-conducting and light emitting polymers. The particulate support containing light emitting polymers may be arranged on display panels.

The 3D macroporous polymer is particularly useful for solid phase synthesis of an organic species, particularly macromolecules. In a preferred embodiment the 3D macroporous polymer may be employed in the synthesis of peptides, oligonucleotides or oligosaccharides.

The 3D macroporous polymer according to the invention simplifies solid phase synthesis through the use of simpler equipment than conventionally employed. The 3D macroporous polymer can be used itself in monolithic form in a column based system. In this instance the polymer forming the 3D macroporous polymer provides the support for solid phase synthesis.

If the 3D macroporous polymer is formed around a traditional polymer support for solid phase synthesis the 3D macroporous polymer can be inert and merely provide a mechanical skeleton to support the traditional polymer for solid phase synthesis.

In the two examples described above the 3D macroporous polymer can be encapsulated within seed beads as described in patent WO2008/012064.

In a preferred embodiment, the cross-linked polymer of the invention is in the form of a 3D macroporous polymer and may be used to immobilize species including proteins, polypeptides, antibodies, oligonucleotides, enzymes, whole cells or fluors. The macroporous polymer may be positioned in an array, with each 3D macroporous polymer in the array being used to assay a different component of a solution. 3D macroporous polymers having ligands covalently attached to their surface or via polymers bound to the surface may be employed in 'wells'. Specific binding of a target ligand such as antigen or complimentary DNA or RNA sequence may then be detected using established methods.

The 3D macroporous polymer of the invention also may be employed to immobilize a biocatalyst. Biocatalysts are often used in columns or in systems with filter plates for separation of the solid phase from the mixture under extraction. The problems observed for solid phase synthesis and chromatography referred to herein may similarly be observed with solid phase extraction. The 3D macroporous polymer of the invention provides similar advantages as afforded in chromatography and solid phase synthesis.

The 3D macroporous polymer of the invention is especially useful in immobilising species including solid phase reagents, metal and other catalysts, bio-catalysts, enzymes, proteins, antibodies including polyclonal and monoclonal antibodies, whole cells and polymers. The invention is particularly advantageous in supporting enzymes, for example the lipase Cal B. The lipase Cal B is commonly employed in the manufacture of biodiesel. Moreover the improved convective flow through the 3D macroporous polymer structures of this invention may be particularly suited to the flow of viscous vegetable oils throughout the matrix and therefore find particular application for biodiesel manufacture.

In yet a further application, the present invention may be used in cell culture. Mass culture of animal cell lines is fundamental to the manufacture of viral vaccines and many products of biotechnology. Biological products produced by recombinant DNA technology in animal cell cultures include enzymes, synthetic hormones, immunobiologicals (monoclonal antibodies, interleukins, lymphokines) and anticancer agents. Many simpler proteins can be produced using rDNA in bacterial cultures; more complex proteins that are glycosylated (carbohydrate-modified) currently must be made in animal cells. An important example of such a complex protein is the hormone erythropoietin. The cost of growing mammalian cell cultures is high, so companies are constantly looking to improve techniques.

Cells can be grown in suspension or as adherent cultures. However, adherent cells require a surface, which may be coated with extracellular matrix components to increase adhesion properties and provide other signals needed for growth and differentiation. Generally cells derived from solid tissues are adherent. Organotypic culture involves growing cells in a three-dimensional environment as opposed to two-dimensional culture dishes. This 3D culture system is biochemically and physiologically more similar to in vivo tissue, but is technically challenging to maintain because of many factors (e.g. diffusion).

The invention described herein allows for preparation of a biodegradable polymer that provides a more natural environment for cell culture whilst providing a biodegradable material that can be engineered to release only naturally occurring amino acids upon degradation. These 3D macroporous polymer structures, commonly referred to as supermacroporous when pores of greater than 100 μm are created, are amenable to rapid cell and nutrient migration under static and convectional conditions. The 3D macroporous polymer structures of this invention can be manufactured or cast in almost any shape or size and therefore provide an important scaffold for regenerative medicine. Gelatin is hydrolyzed collagen where inter and intra chain amide bonds have been hydrolyzed chemically to form soluble peptide chains. Collagen is an ideal and natural environment for cells to adhere and differentiate. The poly-ε-lysine may also be co-polymerized with other proteins, for example gelatin to form a collagen like environment. The invention described herein allows for preparation of a biodegradable polymer that provides a more natural environment for other cell culture applications. The invention may be employed in the culture of algae such as *Botryococcus braunii*, for the production of biofuel. The cross-linked poly-ε-lysine prepared as a 3D macroporous scaffold can provide a readily modified environment for the culture of algae and be designed to be buoyant on the surface of ponds, providing improved access to UV light.

The invention is particular useful in medical diagnostic tests such as immunoassay. Accordingly the invention further provides medical diagnostics for detecting the presence of a compound comprising a particulate support, macroporous support, microporous support or coating according to the invention and a functional material such as an enzyme, for example horseradish peroxidase, supported by the polymer in the support for selectively reacting with or binding to the compound to be detected.

Many medical diagnostics rely upon solid supports to immobilize various diagnostic ligands. The 3D macroporous polymer of the present invention may be used in a medical diagnostic procedure where physical separation of the solid phase through a liquid phase is required.

Diagnostic, screening and compound library applications often use microarray systems. It is possible to combine poly-ε-lysine, cross-linker and activating agents separately through a printer on a range of surfaces to lay down precise arrangements for microarrays. Similarly, a printing technique could be used to prepare an artificial skin for wound care and regenerative medicine.

In a further embodiment the polymer can be fabricated into fibers either through electro-spinning or by traditional techniques for fiber manufacture. Fiber mats, loose fibers or woven fibers will have applications in all of the described fields.

The polymer can also be applied by spraying so it can provide useful coatings for a range of applications including for example antimicrobial and antifungal coatings.

The invention is illustrated by reference to the accompanying drawings in which.

The invention is illustrated by the following non-limiting examples.

EXAMPLE 1—PREPARATION OF SUPERMACROPOROUS CROSS-LINKED POLY-ε-LYSINE

Poly-ε-lysine (200 mg, 1 mmol amine content) was dissolved in DMF/water (2.45 cm$^3$, 1:1 v/v) and NMM (0.137 cm$^3$, 1.2 mmol) added followed by glutaric anhydride (70 mg, 0.6 mmol of glutaric anhydride i.e. an excess relative to the amine). The reaction was allowed to proceed for 2 hours.

N-Hydroxysuccinimide (143 mg) was added followed by Expancel 920 DEX 80 d30 (80 μm polyacrylonitrile balloons) (50 mg, ~3 cm$^3$) and EDCl (224 mg, 1.2 mmol) was added to initiate polymerisation. The mixture was mixed thoroughly for 1 minute cast into a sheet on a polypropylene surface before cutting into discs using a cork borer. The polymerisation was left to go to completion overnight at room temperature.

Figure 1:
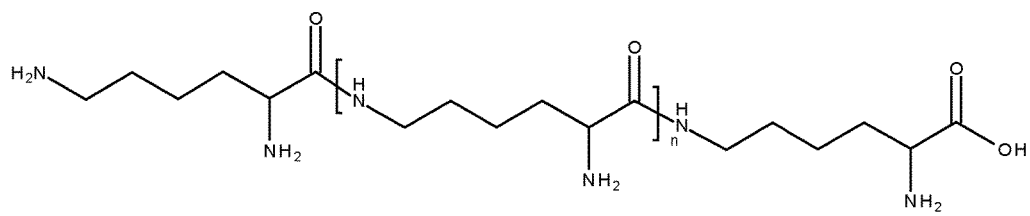
FIG. 1 shows a diagrammatic representation of poly-ε-lysine.
Figure 2:
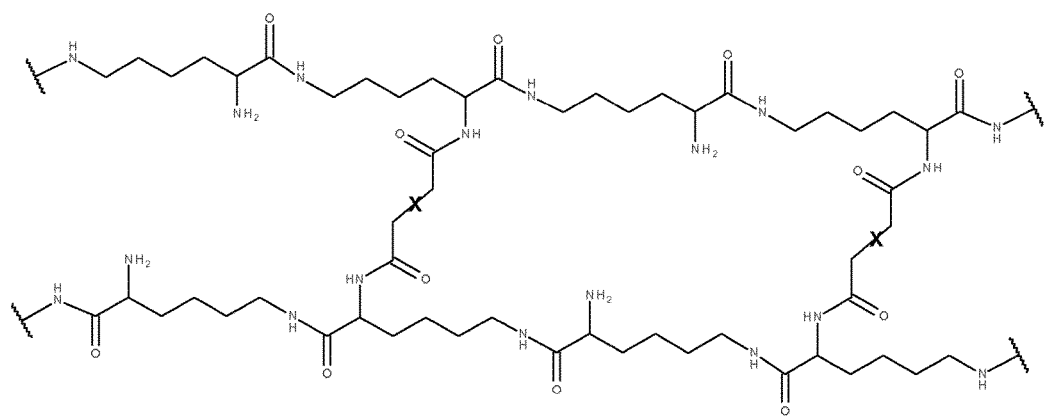
FIG. 2 shows a diagrammatic representation of poly-ε-lysine cross-linked with a bifunctional carboxylic acid.
Figure 3:
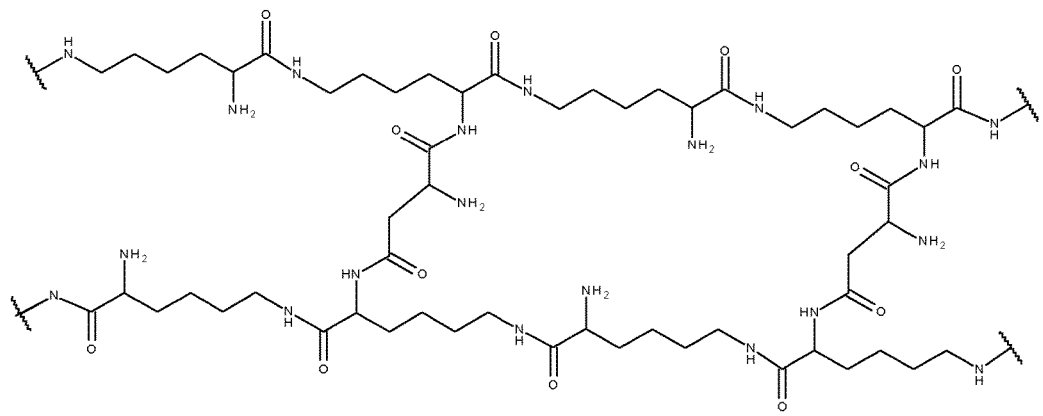
FIG. 3 shows a diagrammatic representation of poly-ε-lysine cross-linked with aspartic acid as example.
Figure 4:
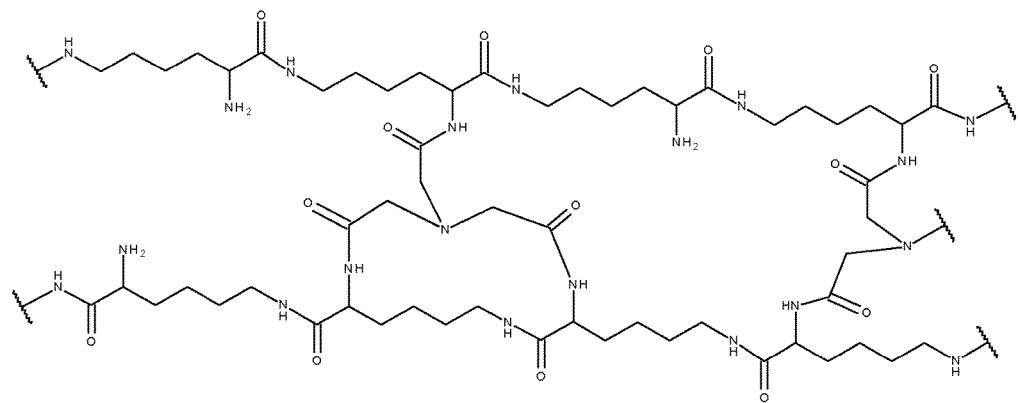
FIG. 4 shows a diagrammatic representation of poly-ε-lysine cross-linked with cystine.
Figure 5:
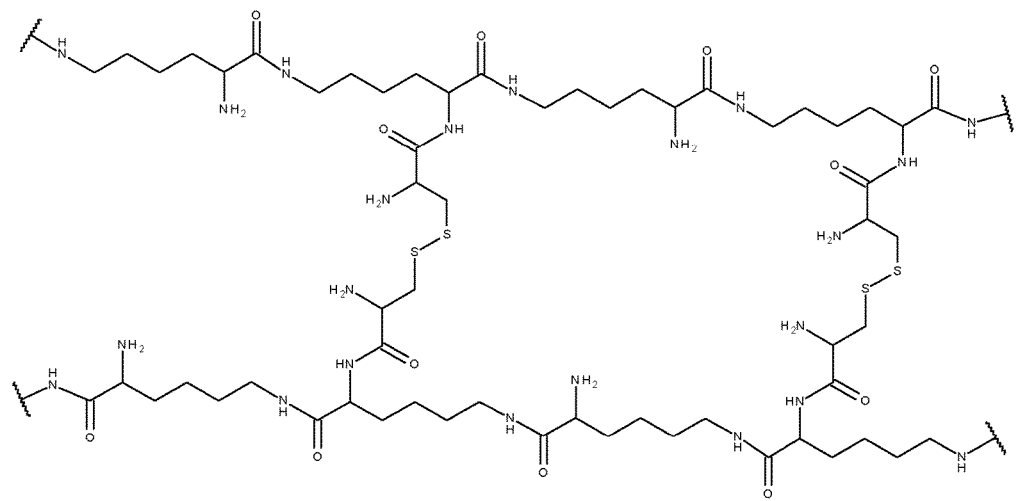
FIG. 5 shows a diagrammatic representation of poly-ε-lysine cross-linked with nitrilotriacetic acid.
Figure 6:
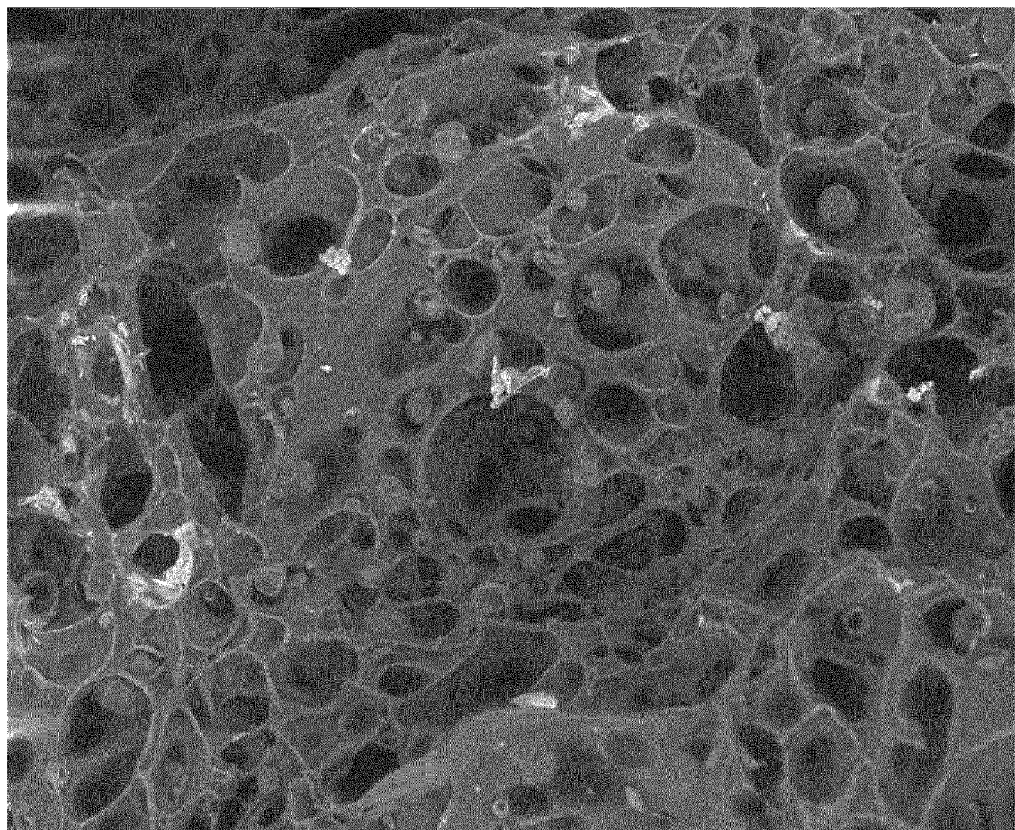
FIG. 6 shows an SEM of the product of Example 1 prior to dissolution of the polyacrylonitrile balloons is shown in FIGS. 7a and 7b show SEM's of the self-assembled supermacroporous sheet of Example 2.

An SEM of the product prior to dissolution of the polyacrylonitrile balloons is shown in FIG. 6. The cavities shown are approximately 20 to 100 microns in size as shown by comparison with the 300 micron scale bar at the bottom right hand portion of the figure.

The discs prepared above were treated with DMF overnight to dissolve the polyacrylonitrile balloons then washed thoroughly with potassium phosphate buffer (100 mmol/dm$^3$, pH 7) and water before freeze drying from water.

The supermacroporous cross-linked poly-ε-lysine has been used shown to support three dimensional growth and proliferation of human embryonic stem cells.

EXAMPLE 2—PREPARATION OF A SELF-ASSEMBLED SUPERMACROPOROUS CROSS-LINKED POLY-ε-LYSINE SHEET

A solution was prepared containing poly-ε-lysine (4.93 g, 28.7 mmol amine content), dodecanedioic acid (3.47 g, 30 mmol carboxyl content) and sodium hydroxide (1.15 g, 28.7 mmol) in water (100 cm$^3$).

A solution of EDCl (14.46 g, 75 mmol) and HONSu (1.65 g, 14 mmol) in water (30 cm$^3$) was added to the above solution and the mixture immediately poured into a tray to form a layer 5 mm deep.

After 20-30 minutes the mixture had solidified to form a 5 mm thick supermacroporous sheet. The sheet was washed thoroughly with water then dried by lyophilisation.

Figure 7A:
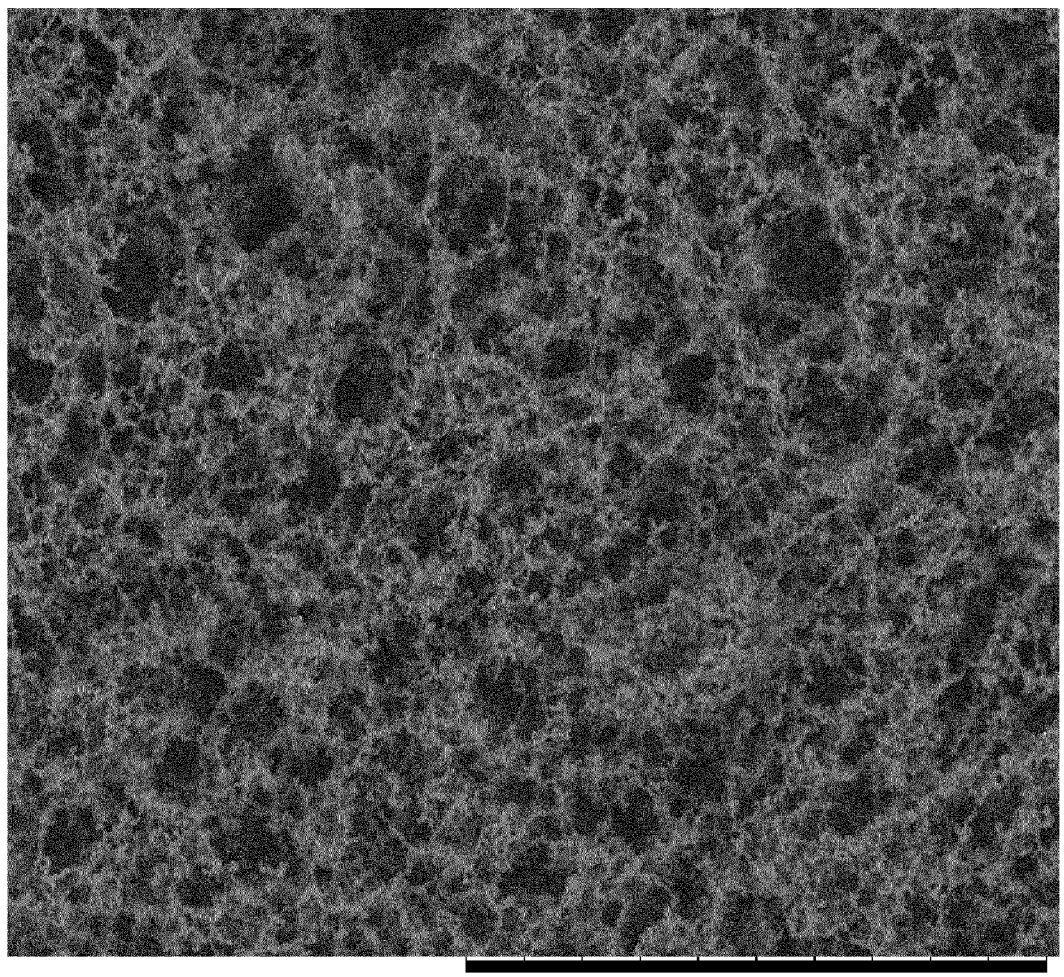
Figure 7B:
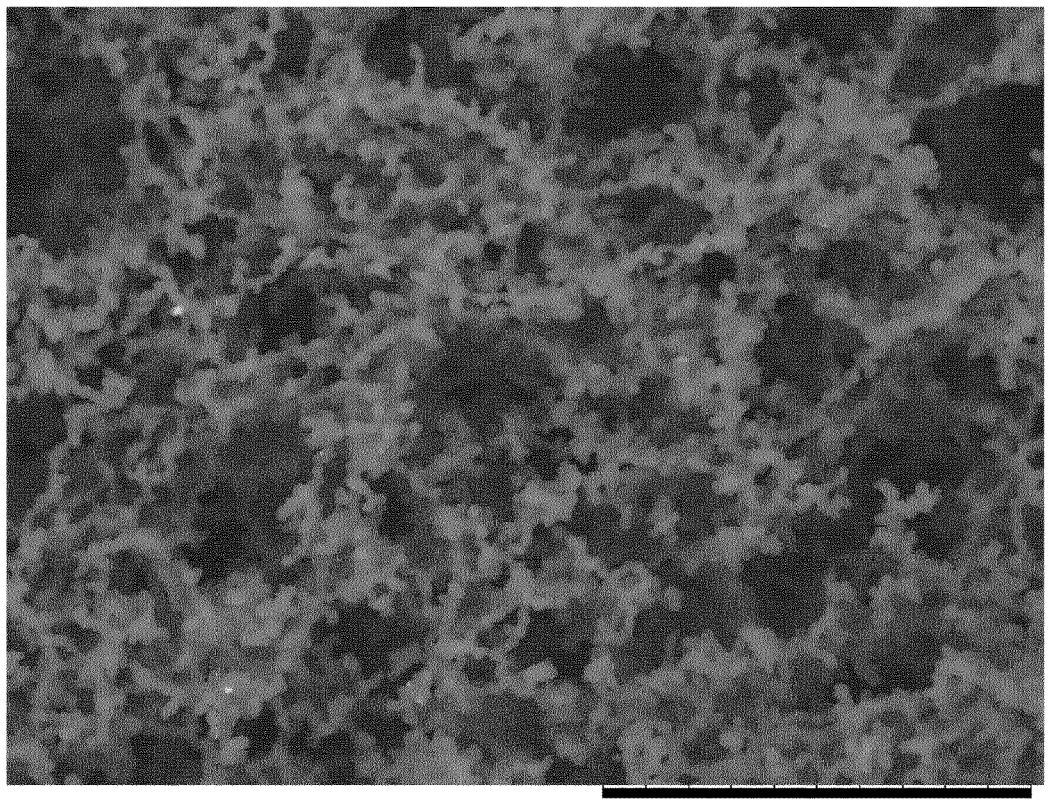

SEM's of the self-assembled supermacroporous sheet is shown in FIGS. 7a and 7b.

EXAMPLE 3—3D CULTURE OF MOUSE EMBRYONIC STEM CELLS (ESC'S) ON SELF-ASSEMBLED SUPERMACROPOROUS CROSS-LINKED POLY-ε-LYSINE

Supermacroporous discs cut from the above sheet were washed with phosphate buffered saline (3×PBS) and UV irradiated for 30 min prior to cell contact.

The discs were seeded with mouse embryonic stem cells and cultured in Advanced™ high glucose DMEM (Gibco, Invitrogen, UK) supplemented with 1 mM 3-mercaptoethanol (Gibco, Invitrogen, UK), 2 mM L-glutamine (Gibco, Invitrogen, UK), 1000 U/mL leukaemia inhibitory factor (LIF) (Millipore, UK) and 2% fetal calf-serum (PAA). This medium was changed every second day.

Immuno-staining of ESCs in contact with polymer involved fixing cells in 4% paraformaldehyde (PFA), followed by washing with PBS (3×). Cells were incubated with blocking solution (10% fetal calf serum, 0.1% Triton X-100 in PBS) at RT for 40 min. Blocking solution was removed and primary antibody solution was added (Oct4/Nanog), cells were incubated at 4° C. overnight. Cells were washed (3×PBS), and secondary antibody solution was added and incubated at RT for 2 h, after which cells were washed (3×PBS), and counterstained with nuclei marker, DAPI (1 cm$^3$ DAPI: 1 μL (¹/₁₀₀** working stock+1 mL PBS), incubated at RT in dark for 5 min. Cells were washed three times in PBS and mounted on a slide with a coverslip and fluorescent mountant.

Figure 8A:
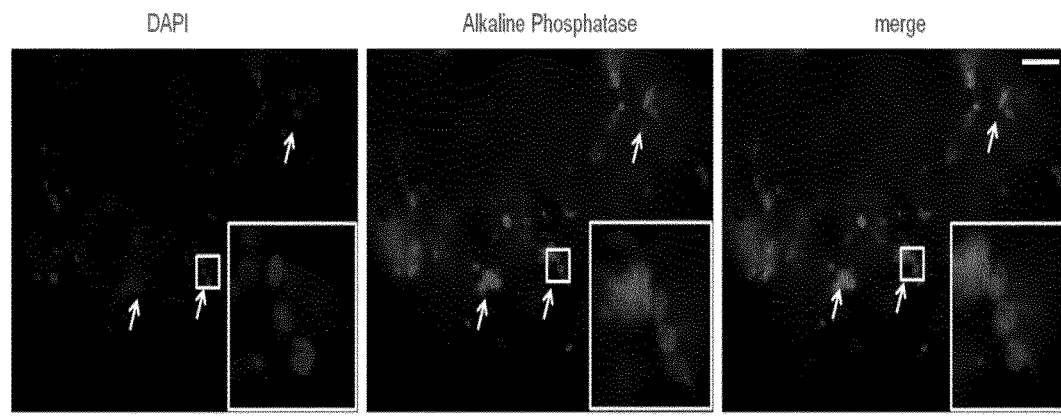
FIGS. 8a, 8b and 8c show sectioned samples of the stained cells showing proliferation throughout the polymer of Example 3.
Figure 8B:
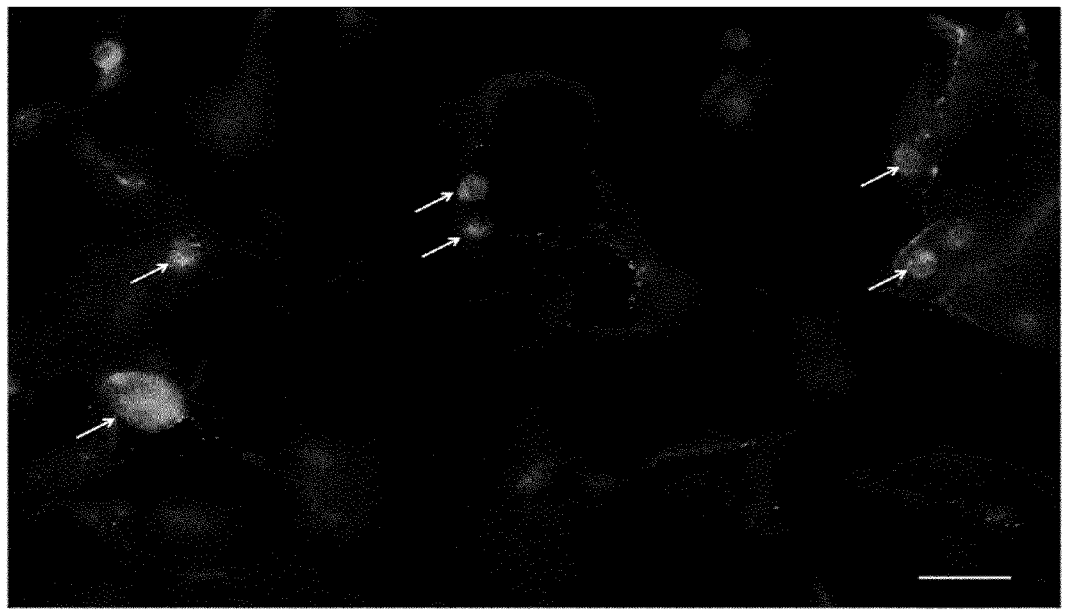
Figure 8C:
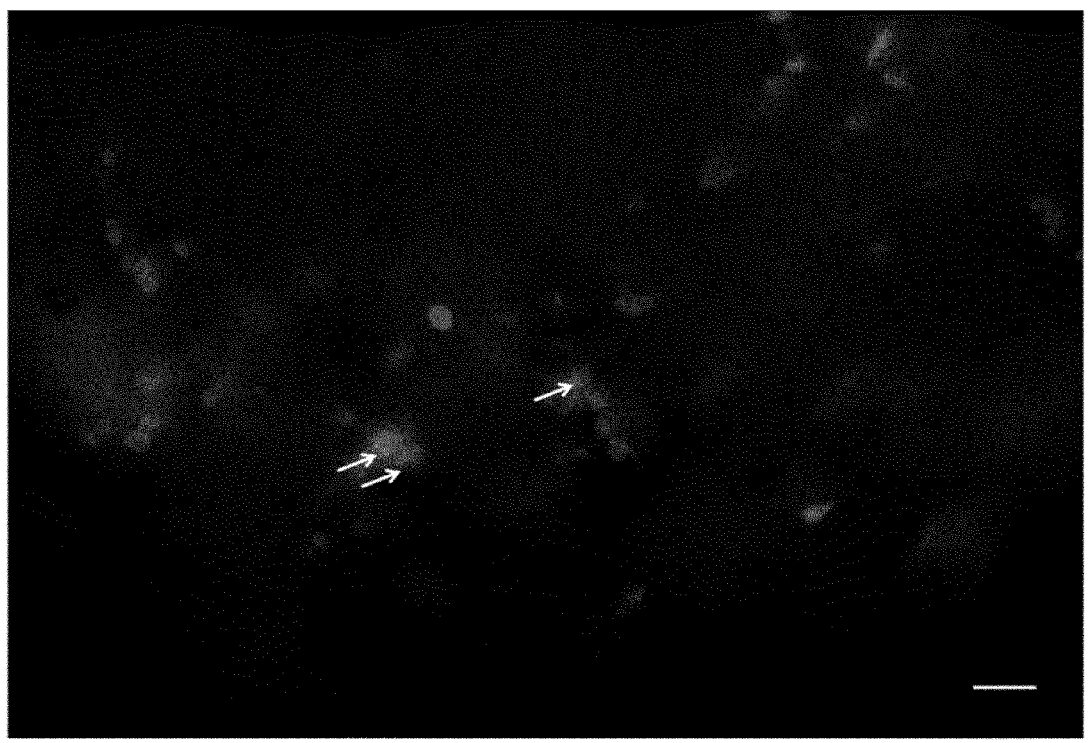

Sectioned samples of the stained cells showing proliferation throughout the polymer are shown in FIGS. 8a, 8b and 8c.

ESCs were seeded onto polymers, to determine ESC attachment and, most importantly the effect the polymer has on ESC self-renewal over time.

In FIG. 8a ESCs were seeded onto super macroporous polymers and allowed to proliferate for 7 days. After 7 days, ESCs and polymers were fixed, gelatine embedded, frozen and sectioned, before co-staining with DAPI (blue) and alkaline phosphatise (red). The polymer supports ESC viability and attachment, and ESCs retain alkaline phosphatase expression. Scale bar represents 100 μm and images are representative of entire population. The experiment was repeated 3 times.

For FIG. 8b ESCs were seeded onto supermacroporous polymers and allowed to proliferate for 7 days. After 7 days, ESCs and polymers were fixed, gelatine embedded, frozen and sectioned, prior to staining with self-renewal marker, nanog (green). The polymer is shown to support ESC attachment; furthermore ESCs remain positive for nanog, thus maintain the capacity to self-renew. Scale bar represents 25 um. Images are representative of entire population.

In FIG. 8c ESCs were seeded onto supermacroporous polymers and allowed to proliferate for 7 days. After 7 days, ESCs and polymers were fixed, gelatine embedded, frozen and sectioned, prior to co-stain with self-renewal marker Oct4 (red) and nuclei marker DAPI (blue). The polymer supports ESC attachment, furthermore ESCs remain positive for Oct4, therefore maintaining the capacity to self-renew. Scale bar represents 50 um. Images are representative of entire population.

The polymer supported ESC attachment and furthermore ESCs retained the expression of alkaline phosphatase for up to 7 days. Similarly, ESCs maintained the expression of self-renewal markers, transcription factors, Nanog and Oct4 after 7 days. Collectively, this suggests that this specific polymer not only supports ESC viability but supports maintenance of ESC pluripotency, crucial in any ESC scale-up culture condition.

EXAMPLE 4—3D CULTURE OF KIDNEY CELLS ON SELF-ASSEMBLED SUPERMACROPOROUS CROSS-LINKED POLY-ε-LYSINE

Supermacroporous discs cut from the above sheet were washed with phosphate buffered saline (3×PBS) and UV irradiated for 30 min prior to cell contact.

The discs were seeded with kidney stem cells (KSC's) and cultured in high glucose DMEM (Gibco, Invitrogen, UK) supplemented with 10% fetal calf serum (PAA), 2 mM L-glutamine (Gibco Invitrogen, UK), 1% NEAA (Gibco, Invitrogen, UK), 1 mM 2-β-mercaptoethanol (Gibco Invitrogen, UK). This medium was changed every second day.

KSCs (GFP stained) were seeded onto the polymer and attachment/interaction monitored. Initially at day 1, KSCs remained rounded on the surface, however at day 10, KSCs morphology appears typically flattened around the surface of the polymer.

Figure 9:
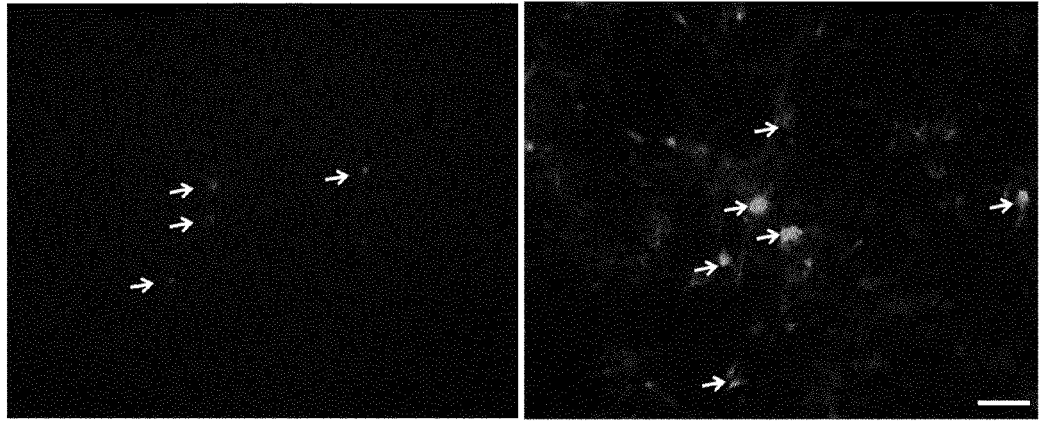
FIG. 9 shows sectioned samples of the stained cells showing proliferation throughout the polymer in Example 4.

Sectioned samples of the stained cells showing proliferation throughout the polymer are shown in FIG. 9. KSCs GFP were seeded onto supermacroporous polymer and attachment/interaction monitored. Initially at day 1, KSCs remained rounded on the surface, however at day 10, KSCs morphology appears typically flattened around the surface of the polymer.

EXAMPLE 5—CULTURE OF SCHWANN NERVE CELLS ON SELF-ASSEMBLED SUPERMACROPOROUS CROSS-LINKED POLY-ε-LYSINE

Samples of the supermacroporous polymer were placed in triplicate into wells of a 12 well tissue culture plate and UV sterilized for 1 hour prior to hydrating the samples in Schwann cell growth medium [SCGM (DMEM+10% FBS+GGF+forskolin)]. Two cell densities were seeded (500,000 and 50,000 Schwann cells) onto each of the supermacroporous polymer scaffolds in SCGM. The Alamar blue absorbance assay was used to test cell proliferation.

Alamar blue results show that Schwann cells initially attach and survive in the supermacroporous polymer scaffolds after 24 hours. Overall cell proliferation was allowed to progress over a 5 day period in all samples tested.

In summary, initial Schwann cell attachment and growth was demonstrated by the reduction of Alamar blue at 24 hours on all samples tested. All of the materials tested supported longer-term survival of Schwann cells and are therefore suitable biomaterial for supporting nerve regeneration.

EXAMPLE 6—PREPARATION OF A SELF-ASSEMBLED SUPERMACROPOROUS CROSS-LINKED POLY-ε-LYSINE TUBE

A solution was prepared containing poly-ε-lysine (4.93 g, 28.7 mmol amine content), dodecanedioic acid (3.47 g, 30 mmol carboxyl content) and sodium hydroxide (1.15 g, 28.7 mmol) in water (100 cm3).

A solution of EDCl (14.46 g, 75 mmol) and HONSu (1.65 g, 14 mmol) in water (30 cm3) was added to the above solution and the mixture immediately poured into a tubular mould.

After 20-30 minutes the mixture had solidified to form a tube of 15 mm external diameter with a wall thickness of 5 mm. The tube was washed thoroughly with water then dried by lyophilisation.

Figure 10:
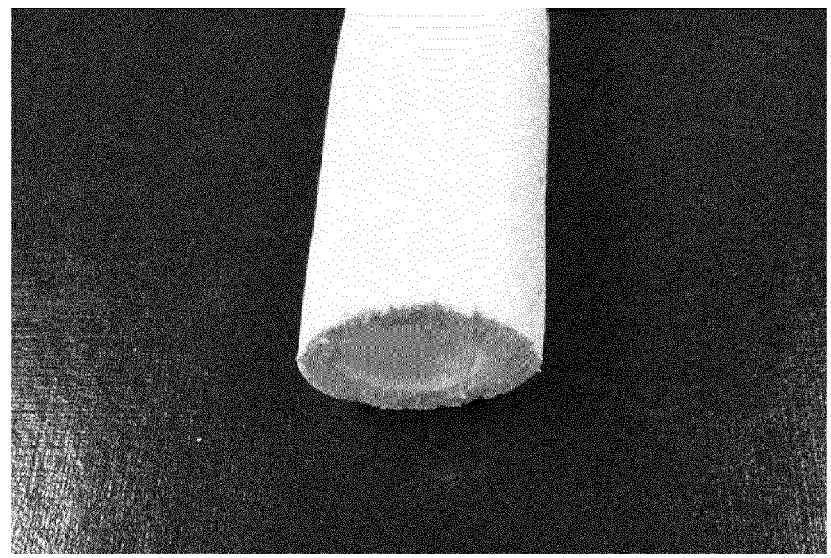
FIG. 10 shows a photograph of the self-assembled supermacroporous tube from Example 6.

A photograph of the self-assembled supermacroporous tube is shown in FIG. 10.

EXAMPLE 7—PREPARATION OF A SUPERMACROPOROUS COLUMN MONOLITH FOR CHROMATOGRAPHIC SEPARATIONS

A solution was prepared containing poly-ε-lysine (0.49 g, 2.9 mmol amine content), dodecanedioic acid (0.35 g, 3.0 mmol carboxyl content) and sodium hydroxide (0.115 g, 2.9 mmol) in water (10 $cm^3$).

A solution of EDCl (1.45 g, 7.5 mmol) and HONSu (0.165 g, 1.4 mmol) in water (3 $cm^3$) was added to the above solution and the mixture immediately used to fill an empty HPLC column (4.6 mm diameter×10 cm).

After 20-30 minutes the mixture had solidified to form a monolith. The monolith was washed thoroughly with water on an HPLC system.

EXAMPLE 8—IMMOBILISATION OF PROTEIN A ON CROSS-LINKED POLY-ε-LYSINE SUPERMACROPOROUS COLUMN MONOLITH FOR ANTIBODY PURIFICATION COUPLING OF RPROTEIN A TO CROSS-LINKED POLY-ε-LYSINE

N-hydroxysuccinimide (1 g) was dissolved in cold MES buffer (25 mmol/$dm^3$, pH 5.0, 2.5 $cm^3$) and mixed with EDCl (1 g) dissolved in MES buffer (25 mmol/$dm^3$, pH 5.0, 2.5 $cm^3$). This solution was passed through the monolith using an HPLC pump. The monolith was washed with MES buffer (25 mmol/$dm^3$, pH 5.0, 50 $cm^3$) and immediately, a solution of rProtein A (5 $cm^3$, 4 mg/$cm^3$ in 25 mmol/$dm^3$ MES, pH 5.0) was passed onto the column and allowed to stand overnight. The monolith was washed with Trizma-HCl (30 $cm^3$ pH 7.4) to block any remaining N-hydroxysuccinimide esters on the polymer. The monolith was washed with water (100 $cm^3$) and stored in water.

The Protein A based monolith was tested to determine whether it retained Human IgG under standard conditions known to those skilled in the art. The column was shown to retain Human IgG as expected.

EXAMPLE 9—PREPARATION OF AN ELECTROSPUN FIBRE

A solution containing polyacrylonitrile (0.8 g, 150,000 average molecular weight), poly-ε-lysine (0.4 g) and sebacic acid (0.24 g) in DMSO (6 $cm^3$), was electrospun (24 kV, 0.5 $cm^3$/hr) on to a roller drum at 40° C. and 30% humidity.

A portion (5 cm2) of the electrospun fibre mat produced was treated with an aqueous solution of EDCl (1 g in 5 $cm^3$ of water) for 1 h then washed thoroughly with water. The resulting cross-linked fibre mat was washed thoroughly with N,N-dimethylformamide to remove the PAN support, then it was washed with methanol before drying in air.

Figure 11:
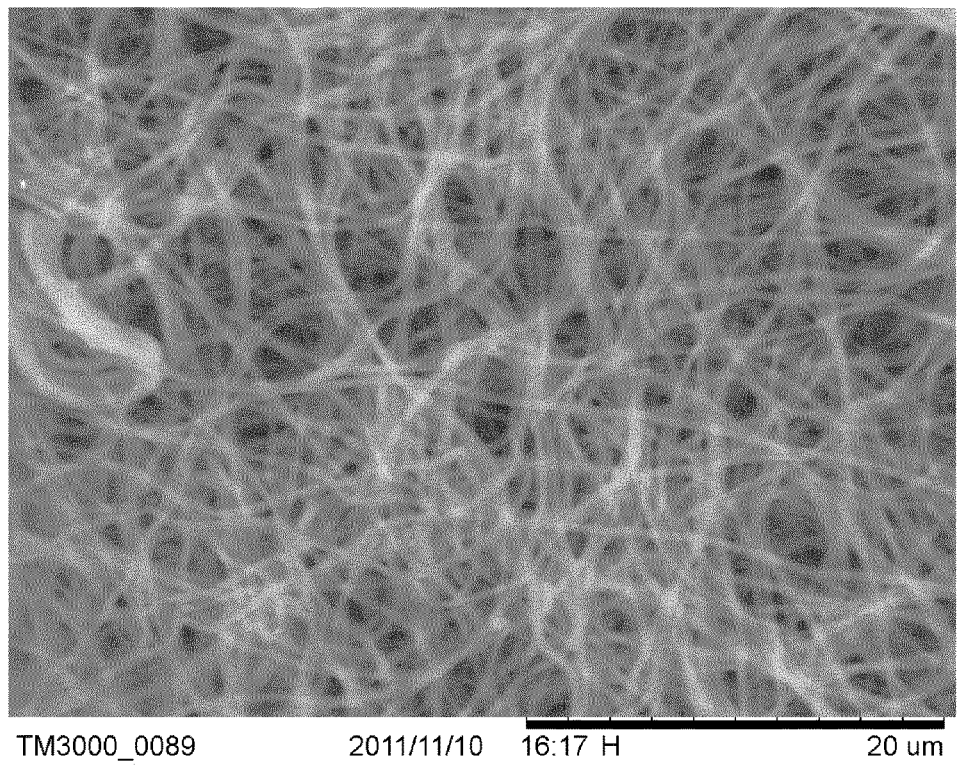
FIG. 11 shows an SEM of the resulting cross-linked nanofibre mat from Example 9.

An SEM of the resulting cross-linked nanofibre mat is shown in FIG. 11.

EXAMPLE 10—PREPARATION OF AN OPTICALLY CLEAR LENS

A solution was prepared containing poly-ε-lysine (0.49 g, 2.9 mmol amine content), sebacic acid (0.15 g, 1.45 mmol carboxyl content) and sodium hydroxide (0.06 g, 1.5 mmol) in water (1.5 $cm^3$).

A solution of EDCl (0.83 g, 4.35 mmol) in water (1 $cm^3$) was added to the above solution and the mixture immediately used to fill the base of polypropylene test tubes to demonstrate the ability to cast a lens.

After 20-30 minutes the mixture had solidified to form a clear polymer resembling a contact lens. The lens was washed thoroughly with water then left to dry in air.

Figure 12:
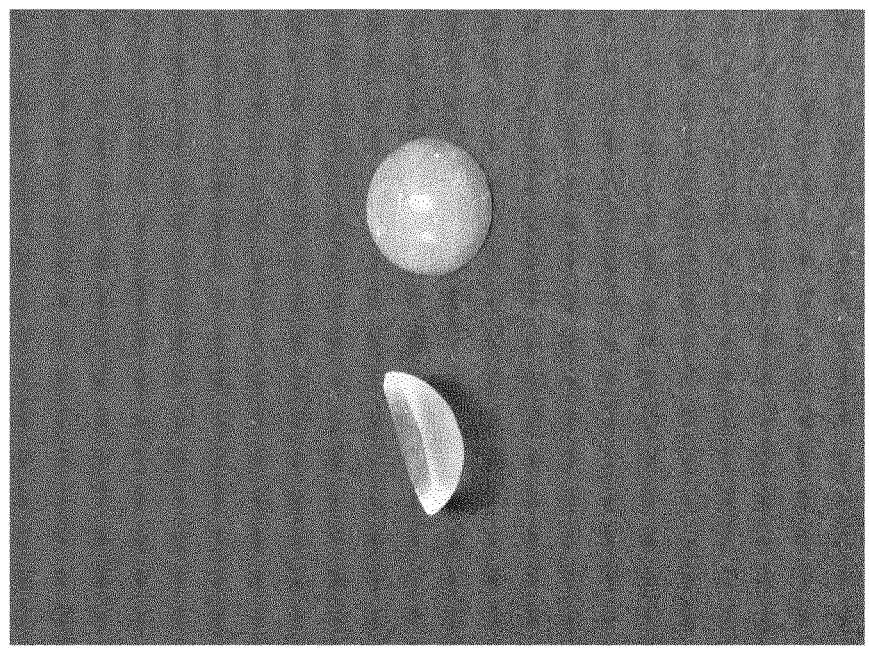
FIG. 12 shows a photograph of the lens of Example 10.

A photograph of the lens is shown in FIG. 12.

The invention claimed is:

1. A non-particulate cross-linked poly-ε-lysine polymer comprising poly-ε-lysine and a cross-linker, wherein the poly-ε-lysine and cross-linker are conjugated via amide bonds, wherein the cross-linker comprises at least two functional groups capable of reacting with an alpha carbon amine of poly-ε-lysine, and the cross-linker is selected from: a moiety derived from a compound of formula $X[CO_2H]_n$, where n is 2 or more and X is an aliphatic chain; a bis-carboxy-polyalkylene glycol; nitrilotriacetic acid; glutaric acid; an amino acid; EDTA; a synthetic peptide containing the tripeptide sequence -Arg-Gly-Asp-; and $HOOCCH_2CH_2CONHCH_2CH_2OCH_2CH_2OCH_2CH_2OCH_2CH_2NHCO$ $CH_2CH_2COOH$.

2. The poly-ε-lysine polymer according to claim 1 wherein the cross-linker comprises a moiety derived from a compound of formula $X[CO_2H]_n$ where n is 2 or more and X is a hydrophobic or hydrophilic linking group having a molecular weight of 14 to 250 excluding any functional substituents on the linking group.

3. The poly-ε-lysine polymer according to claim 1 which is insoluble in water.

4. The poly-ε-lysine polymer according to claim 1 which is porous.

5. The non-particulate support comprising the poly-ε-lysine polymer according to claim 1.

6. The non-particulate support according to claim 5 wherein the cross-linked poly-ε-lysine support is used to coat a macro form directly or indirectly.

7. The non-particulate support according to claim 5 wherein the cross-linked poly-ε-lysine support is used to coat and is bound covalently to a macro form.

8. The non-particulate support according to claim 5 wherein the cross-linked poly-ε-lysine is used to coat an organic macro form.

9. The non-particulate support according to claim 5 wherein the cross-linked poly-ε-lysine is used to coat an inorganic macro form.

10. The non-particulate cross-linked poly-ε-lysine based support according to claim 5 wherein the cross-linked poly-ε-lysine is functionalised to provide a material comprising a catalyst, an initiator species for peptide synthesis, an initiator species for oligonucleotide synthesis, an initiator species for solid phase organic synthesis, a pharmaceutical active, an agrochemical active, a surface for chromatographic separation, a species to promote cell culture or differentiation, a protein or other biological macromolecule.

11. The three dimensional structure comprising a cross-linked poly-ε-lysine according to claim 1.

12. The three dimensional structure according to claim 11 in which the structure is microporous, macroporous or a fiber.

13. The three dimensional macroporous structure according to claim 11 coated with cross-linked poly-ε-lysine wherein the cross-linked poly-ε-lysine used to coat is bound covalently to the microporous, macroporous or a fiber structure directly or indirectly.

14. The three dimensional macroporous structure according to claim 11 coated with cross-linked poly-ε-lysine wherein the cross-linked poly-ε-lysine used to coat is not bound covalently to the microporous, macroporous or a fiber structure.

15. The three dimensional cross-linked poly-ε-lysine based support according to claim 11 wherein the cross-linked poly-ε-lysine is functionalised to provide a material comprising a catalyst, an initiator species for peptide synthesis, an initiator species for oligonucleotide synthesis, an initiator species for solid phase organic synthesis, a pharmaceutical active, an agrochemical active, a surface for chromatographic separation, a species to promote cell culture or differentiation, a protein or other biological macromolecule.

16. The sheet, article or fibre comprising a polymer according to claim 1 or a support according to claim 5.

17. The wound treatment product comprising a polymer according to claim 1 or a support according to claim 5 and a component or a composition for treating a wound or a therapeutic agent.

18. The wound treatment product according to claim 17 wherein the polymer or support is in the form of a sheet.

19. The non-particulate support according to claim 5, for use in a medical diagnostic application, further comprising a functional material bound or retained by the support.

20. The non-particulate support for use in a medical diagnostic application according to claim 19, wherein the functional material comprises an enzyme supported by the polymer.

21. The poly-ε-lysine polymer according to claim 2 wherein the cross-linker comprises two or more carboxylic acid groups and an aliphatic chain linking the two or more groups.

22. The poly-ε-lysine polymer according to claim 3 wherein the cross-linker comprises a bis carboxylic acid, wherein the two carboxylic acid groups of the bis carboxylic acid are linked by a hydrocarbon group comprising 2 to 14 carbon atoms.

23. The poly-ε-lysine polymer according to claim 1 wherein the cross-linker is a moiety derived from a compound of formula $X[CO_2H]_n$, where n is 2 or more, and wherein X is a linear or branched hydrocarbyl group.

* * * * *